(12) United States Patent
Hosemann

(10) Patent No.: US 11,452,487 B2
(45) Date of Patent: Sep. 27, 2022

(54) X-RAY DETECTOR MODULE, MEDICAL IMAGING DEVICE AND METHOD FOR OPERATING AN X-RAY DETECTOR MODULE

(71) Applicant: Siemens Healthcare GmbH, Erlangen (DE)

(72) Inventor: Michael Hosemann, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 17/411,279

(22) Filed: Aug. 25, 2021

(65) Prior Publication Data
US 2022/0061778 A1 Mar. 3, 2022

(30) Foreign Application Priority Data
Aug. 31, 2020 (DE) ...................... 10 2020 210 954.0

(51) Int. Cl.
*A61B 6/03* (2006.01)
*H04N 5/32* (2006.01)
(Continued)

(52) U.S. Cl.
CPC ............... *A61B 6/032* (2013.01); *G01T 1/17* (2013.01); *H04N 5/32* (2013.01); *G01N 23/046* (2013.01);
(Continued)

(58) Field of Classification Search
CPC ....... H04N 5/32; G01T 1/17; G01N 2223/304
See application file for complete search history.

(56) References Cited

U.S. PATENT DOCUMENTS

| 3,717,753 A * | 2/1973 | Thomas ................ G01T 1/2045 250/363.01 |
| 2005/0174144 A1 | 8/2005 | Veredas-Ramirez et al. |

(Continued)

FOREIGN PATENT DOCUMENTS

| DE | 102004006769 B3 | 8/2005 |
| DE | 102016221221 A1 | 5/2018 |

OTHER PUBLICATIONS

German Office Action and English translation thereof dated Apr. 14, 2021.
(Continued)

*Primary Examiner* — Chih-Cheng Kao
(74) *Attorney, Agent, or Firm* — Harness, Dickey & Pierce, P.L.C.

(57) ABSTRACT

An X-ray detector module includes a plurality of evaluation circuits, coupled to at least one converter circuit, each evaluation circuit including a multiplicity of pixel electronics circuits for processing the electrical signals from the converter circuit pixel by pixel; and a number of forwarding circuits, a forwarding circuit including at least a first data input for receiving a measured data set from a first evaluation circuit and at least a second data input for receiving a measured data set from a second evaluation circuit, or for receiving at least one forwarded measured data set from a further forwarding circuit of the number of forwarding circuits. Each forwarding circuit is constructed to forward the measured data sets that are received by way of the first data input and second data input to a coupled receiving circuit over a common data output.

24 Claims, 9 Drawing Sheets

(51) Int. Cl.
  *G01T 1/17* (2006.01)
  *G01N 23/046* (2018.01)
  *H05G 1/00* (2006.01)
(52) U.S. Cl.
  CPC ... *G01N 2223/304* (2013.01); *G21K 2207/00* (2013.01); *H05G 1/00* (2013.01)

(56) References Cited

U.S. PATENT DOCUMENTS

2017/0354389 A1* 12/2017 Eichenseer ............. G01T 1/247
2018/0123716 A1   5/2018 Eismann et al.

OTHER PUBLICATIONS

German Decision to Grant and English translation thereof dated Dec. 9, 2021.
German Office Action dated Apr. 14, 2021.

* cited by examiner

X-RAY DETECTOR MODULE, MEDICAL IMAGING DEVICE AND METHOD FOR OPERATING AN X-RAY DETECTOR MODULE

PRIORITY STATEMENT

The present application hereby claims priority under 35 U.S.C. § 119 to German patent application number DE 102020210954.0 filed Aug. 31, 2020, the entire contents of which are hereby incorporated herein by reference.

FIELD

Example embodiments of the invention generally relate to an X-ray detector module, comprising a plurality of evaluation units and a number of forwarding units; to an evaluation unit for use in an X-ray detector module of this kind; to a medical imaging device, comprising an X-ray detector module; and to a method for operating an X-ray detector module.

BACKGROUND

In X-ray imaging, for example computed tomography, angiography or radiography, direct-conversion X-ray detectors that count or integrating indirect-conversion X-ray detectors may be used.

In direct-conversion X-ray detectors, the X-ray radiation or photons can be converted into electrical pulses by a suitable converter material. Converter materials that may be used are for example CdTe, CZT, CdZnTeSe, CdTeSe, CdMnTe, InP, TlBr2, HgI2, GaAs or others. The electrical pulses are evaluated by an evaluation unit, for example an integrated circuit (application-specific integrated circuit, ASIC). In X-ray detectors that count, incident X-ray radiation is measured by counting the electrical pulses that are triggered by the absorption of X-ray photons in the converter material. The height of the electrical pulse is typically proportional to the energy of the absorbed X-ray photon. This allows an item of spectral information to be extracted by comparing the height of the electrical pulse with a threshold value.

In indirect-conversion X-ray detectors, the X-ray radiation or photons can be converted into light by a suitable converter material and into electrical pulses via photodiodes. Converter materials that are frequently used are scintillators such as GOS (Gd2O2S), CsJ, YGO or LuTAG. Scintillators are used in particular in medical X-ray imaging in the energy range up to 1 MeV. Conventionally, so-called indirect-conversion X-ray detectors, so-called scintillator detectors, are used, in which the X-rays or gamma rays are converted into electrical signals in two stages. In a first stage, the X-ray or gamma quanta are absorbed in a scintillator element and converted into optically visible light; this effect is called luminescence. The light that is excited by luminescence is then, in a second stage, converted into an electrical signal by a first photodiode optically coupled to the scintillator element, and processed further and read off by way of an evaluation unit.

In a detector apparatus for computed tomography systems, data is frequently read off and processed by a considerable multiplicity of evaluation units. In this case, it is also possible to group together a plurality of evaluation units, in particular ASICs, to form a modular unit, wherein these are arranged for example on a common support material or coupled to a common converter unit that comprises the converter material.

SUMMARY

For the configuration and data read-off, data lines to each of the evaluation unit are required. The inventors have discovered that if there is a multiplicity of evaluation units, this results in considerable complexity in the cabling, and in corresponding costs and required space. The inventors have discovered that this also comprises the need to provide space for a sufficiently large number of contacts or for plug connections on the electronic components. This in turn may result in a need to make components, plugs or casing larger and thus likewise in higher costs and more required space. The inventors have discovered that the large amount of space required, including that on the electronic components and support materials, which cannot be put to any other use may moreover provide an obstacle to efficient cooling of the elements if a surface area available for heat dissipation is reduced.

Embodiments of the invention provide an X-ray detector module, an evaluation unit for use in an X-ray detector module of this kind, a medical imaging device, and a method for operating an X-ray detector module that enables less complexity in the cabling.

Further advantageous embodiments and developments of the invention, some of which are inventive in their own right, are set forth in the claims and the description below.

At least one embodiment of the invention relates to X-ray detector module, comprising at least a plurality of evaluation units and a number of forwarding units. The plurality of evaluation units is coupled to at least one converter unit that is constructed to convert incident X-ray radiation into electrical signals. Each evaluation unit of the plurality of evaluation units has a multiplicity of pixel electronics units for processing the electrical signals from the converter unit pixel by pixel, wherein it is possible, based on the processed electrical signals of the multiplicity of pixel electronics units of each evaluation unit of the plurality of evaluation units, to provide a measured data set.

Furthermore, at least one embodiment of the invention relates to an evaluation unit, comprising an integrated forwarding unit, for use in an X-ray detector module according to one of the embodiments described.

Furthermore, at least one embodiment of the invention relates to a medical imaging apparatus, comprising a detection unit with at least one X-ray detector module according to an embodiment of the invention and, arranged opposite this, an X-ray source that is constructed to expose the detection unit, and hence the converter unit coupled to the first plurality of evaluation units of the X-ray detector module, to X-ray radiation.

Furthermore, at least one embodiment of the invention relates to a method for operating an X-ray detector module according to one of the variants described above. The method has the steps of exposure, recording and forwarding.

Furthermore, at least one embodiment of the invention relates to an X-ray detector module, comprising at least one converter, constructed to convert incident X-ray radiation into electrical signals;

a plurality of evaluation circuits, coupled to the at least one converter, each respective evaluation circuit of the plurality of evaluation circuits including a respective multiplicity of pixel electronics to process the electrical signals from the at least one converter pixel by pixel, and based on processed electrical signals of the multiplicity of pixel electronics from each evaluation circuit of the plurality of evaluation circuits, each respective evaluation circuit of the plurality of evaluation circuits being configured to provide a respective measured data set; and a number of forwarding circuits, a forwarding circuit of the number of forwarding circuits, including at least a first data input to receive a first measured data set from a first evaluation circuit of the plurality of evaluation circuits and at least a second data input to receive a second measured data set from a second evaluation circuit of the plurality of evaluation units, or to receive at least one forwarded measured data set from a further forwarding circuit of the number of forwarding circuits, and each respective forwarding circuit of the number of forwarding circuits being constructed to forward measured data sets received via the first data input and second data input to a coupled receiver over a common data output.

Furthermore, at least one embodiment of the invention relates to an evaluation circuit, comprising a forwarding circuit, for use in the X-ray detector module of an embodiment.

Furthermore, at least one embodiment of the invention relates to a medical imaging device, comprising:

at least one detector including at least one of the X-ray detector module of an embodiment and, an X-ray source, arranged opposite the at least one detector, constructed to expose the converter coupled to the first plurality of evaluation circuits to X-ray radiation.

Furthermore, at least one embodiment of the invention relates to the medical imaging device of an embodiment, wherein the medical imaging device is a computed tomography device.

Furthermore, at least one embodiment of the invention relates to a method for operating an X-ray detector module, comprising:

exposing at least one converter circuit of the X-ray detector module, coupled to a plurality of evaluation circuits X-ray detector module, to X-ray radiation via an X-ray source;

recording a measured data set for each evaluation circuit of the plurality of evaluation circuits, based on the incident X-ray radiation; and forwarding the measured data sets via a forwarding circuit of a number of forwarding circuits of the X-ray detector module, wherein at least one of:

a measured data set of the measured data sets, from a first evaluation circuit of the plurality of evaluation circuits is received via a first data input of the forwarding circuit of the number of forwarding circuits of the X-ray detector module, and a measured data set from a second evaluation circuit of the plurality of evaluation circuits, different from the first evaluation circuit, is received via a second data input, and a measured data set the measured data sets, from a first evaluation circuit of the plurality of evaluation circuits is received via of a first data input of the forwarding circuit, and a forwarded measured data set, from a further forwarding circuit of the number of forwarding circuits, is received via a second data input; and the measured data sets that received via at least one of the first data input and second data input are forwarded to a receiving circuit via the forwarding circuit over a common data output.

BRIEF DESCRIPTION OF THE DRAWINGS

The invention is explained below by way of example embodiments, with reference to the attached figures. The illustration in the figures is schematic, highly simplified and not necessarily to scale. In the figures.

DETAILED DESCRIPTION OF THE EXAMPLE EMBODIMENTS

Figure 1:
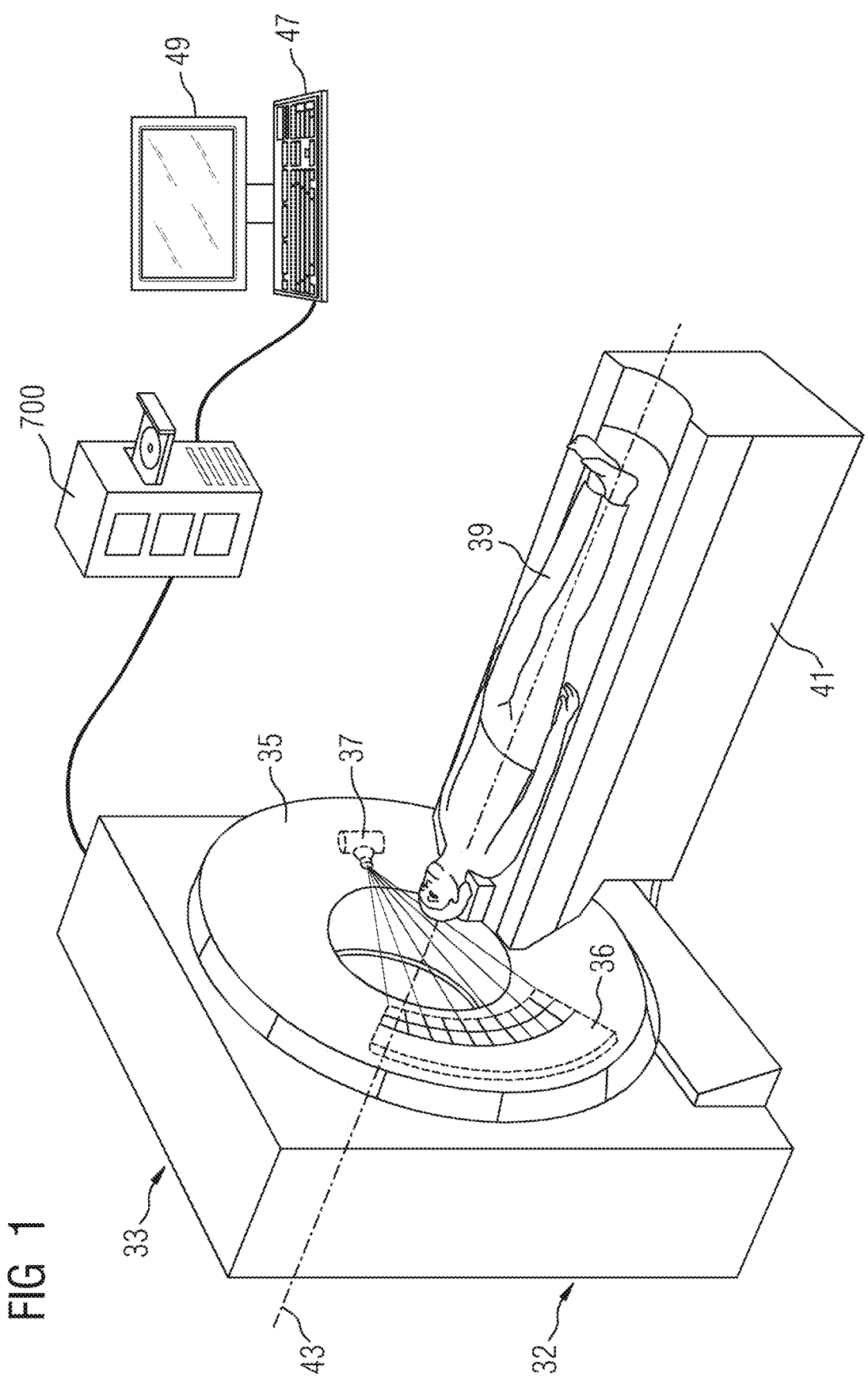
FIG. 1 shows an example embodiment of a medical imaging device.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/ DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes;

etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to X-ray detector module, comprising at least a plurality of evaluation units and a number of forwarding units. The plurality of evaluation units is coupled to at least one converter unit that is constructed to convert incident X-ray radiation into electrical signals. Each evaluation unit of the plurality of evaluation units has a multiplicity of pixel electronics units for processing the electrical signals from the converter unit pixel by pixel, wherein it is possible, based on the processed electrical signals of the multiplicity of pixel electronics units of each evaluation unit of the plurality of evaluation units, to provide a measured data set.

A forwarding unit of the number of forwarding units either has at least a first data input for receiving a measured data set from a first evaluation unit of the plurality and a second data input for receiving a measured data set from a second evaluation unit, different from the first, of the plurality, or it has at least a first data input for receiving a measured data set from a first evaluation unit of the plurality and a second data input for receiving at least one forwarded measured data set from a further forwarding unit of the number of forwarding units.

Furthermore, each forwarding unit of the number of forwarding units is constructed to forward the measured data sets that are received by way of the first data input and second data input to a coupled receiving unit over a common data output. The receiving unit can then be coupled to the forwarding unit over the common data output by way of a data line. The measured data that is received from the forwarding unit can in this way be forwarded by way of a common data line.

To put it another way, each forwarding unit of the number can have at least a first data input, a second data input and a common data output and be constructed to receive, by way of the first data input, at least one measured data set from a first evaluation unit of the plurality, to receive, by way of the second data input, either at least one measured data set from a second evaluation unit, different from the first, of the plurality or at least one measured data set from an evaluation unit of the plurality that is forwarded by a further forwarding unit of the number of forwarding units, and to forward the measured data sets that are received by way of the first data input and second data input by way of a common data output to a coupled receiving unit.

A forwarding unit may in particular be constructed to receive a measured data set by way of the first data input or the second data input in that a data line is formed between a corresponding data input of the forwarding unit and a data output of an evaluation unit of the plurality of evaluation units or the data output of a further forwarding unit of the number of forwarding units.

A forwarding unit of the number may also have more than two data inputs for receiving measured data sets.

If the number of forwarding units comprises a plurality of forwarding units, then the number of forwarding units may comprise both a forwarding unit that has at least a first data input for receiving a measured data set from a first evaluation unit of the plurality of evaluation units and a second data input for receiving a measured data set from a second evaluation unit, different from the first, of the plurality of evaluation units, and also a forwarding unit that has at least a first data input for receiving a measured data set from a first evaluation unit of the plurality of evaluation units and a second data input for receiving at least one forwarded measured data set from a further forwarding unit of the number of forwarding units.

As well as the number of forwarding units that are constructed to receive measured data sets at least by way of a first and a second data input, it is possible for an X-ray detector module also to comprise one or more forwarding units that receive a measured data set only by way of one data input. This may be the case if only one data input is coupled to an evaluation unit of the plurality of or a further forwarding unit by way of a data line. In this case too, a forwarding unit of this kind may in principle take the same form as a forwarding unit of the inventive number of forwarding units but have at least one uncoupled and hence unused data input, with the result that no measured data sets are received by way of this.

The receiving unit may comprise a further forwarding unit of the number of forwarding units or correspond thereto, and be constructed to receive the forwarded measured data set at least by way of a second data input and itself to forward it to a further receiving unit by way of a common data output. However, the receiving unit may also take a different form. For example, the receiving unit may take the form of a read-off unit associated with the X-ray detector module. A read-off unit of this kind may in particular be a modular unit that is placed downstream of the plurality of evaluation units and is constructed to receive the measured data sets of all the evaluation units of the plurality. The read-off unit may be constructed to provide the received measured data sets of all the evaluation units of the plurality for reading off for example at an external processing unit. The read-off unit may take the form of a read-off board, in particular a multilayer read-off board. The read-off unit may have circuits that performs interim further processing of the measured data sets. This may comprise for example compression of the measured data for simplified data transmission, or indeed correction of the measured data. The read-off unit may comprise for example one or more field programmable gate arrays (FPGAs) that is/are configured to receive measured data sets of the plurality of evaluation units and/or to perform the interim further processing of the measured data set. A read-off unit of this kind may moreover also be coupled to a plurality of X-ray detector modules each comprising a plurality of evaluation units.

The X-ray detector module may be a direct-conversion or indirect-conversion X-ray detector module. This means that the at least one converter unit may comprise direct-conversion converter material such as CdTe, CZT, CdZnTeSe, CdTeSe, CdMnTe, InP, TlBr2, HgI2, GaAs or others. In the case of an indirect-conversion X-ray detector, the converter unit may comprise for example a scintillator material. A photodiode matrix may be arranged adjoining the scintillator material.

The plurality of evaluation units that is described here may be coupled to a common converter unit of flat construction. In this case, a plurality of evaluation units that are relatively small in terms of their surface extent may be associated with a relatively large, continuous converter unit. Advantageously, relatively small evaluation units can be provided at lower cost. However, constructions in which in each case only some or indeed only one of the plurality of evaluation units described here is coupled to a respective converter unit are also possible. The plurality of evaluation units may form a modular unit. The plurality of evaluation units described here may form a modular unit with the converter unit or units. The evaluation units of the plurality may also be arranged on a common support unit. For example, the support layer may comprise a support ceramic or a support board or similar. A support unit may take on a structurally stabilizing function, or may also take on functions of data forwarding from the evaluation units to a read-off unit.

The plurality of evaluation units that is described here comprises at least two evaluation units. For example, the plurality comprises four or six evaluation units. The plurality may also comprise more than six evaluation units.

The evaluation units of the plurality of evaluation units may take the form of an integrated circuit, in particular an application-specific integrated circuit (ASIC).

An X-ray detector module according to the invention may comprise, as well as the at least one (first) plurality, also one or more further pluralities of evaluation units and converter units that are associated therewith. The further plurality or pluralities may then take a form that is substantially similar or the same as the at least one (first) plurality.

A respective evaluation unit of the plurality of evaluation units is coupled by way of electrically conductive connections to the converter unit associated therewith. Typically, an electrically conductive connection may be associated with each pixel electronics unit of the multiplicity of pixel electronics units in an evaluation unit. However, constructions in which some of the pixel electronics units have no connection with a converter unit are also possible.

Preferably, the pixel electronics units are constructed to process, pixel by pixel, the signals that are fed by way of the electrically conductive connection from the converter unit associated therewith. Pixel-by-pixel processing in particular enables spatially resolved measurement of the incident X-ray radiation. The pixel electronics units of an evaluation unit of the plurality may also be designated electronics pixels. In addition, connections may also be made between pixel electronics units of an evaluation unit, which enables the signals processed in the respective pixel electronics units to be offset against one another or grouped or adapted in relation to one another.

The pixel electronics units may in particular be constructed to digitize the typically analog signals that are fed from the associated converter unit, with the result that, after processing of the electrical signals by the multiplicity of pixel electronics units of a respective evaluation unit, it is possible to provide a digital measured data set on the basis of the measured and processed signals in the multiplicity of pixel electronics units of an evaluation unit. The measured data set may comprise the digitized measured data from a plurality of pixel electronics units of an evaluation unit. If for example each pixel electronics unit of an evaluation unit provides a respective processed, digital signal, then the measured data set from an evaluation unit can comprise the processed, digital signals of all the pixel electronics units of the evaluation unit that have been collected during a read-off time window—that is to say typically between two successive reads. Based on this measured data, it is possible to generate an X-ray image data set, for example by way of an image reconstruction algorithm.

It is possible for a measured data set from an evaluation unit of the plurality of evaluation units to be transmitted as a complete data bundle in the course of reading off the measured data. This means that in each case all the measured data belonging to the measured data set can be read off/transmitted cohesively. However, configurations in which the measured data of a measured data set is transmitted divided into sub-units—that is, in multiple parts—are also possible. It is then possible for the sub-units to be associated again after transmission, to give a measured data set from an actual evaluation unit, for example only once a read-off unit is reached.

Preferably, the measured data set or the sub-units is/are identifiable, such that the measured data set can be associated with an evaluation unit or the sub-units of a measured data set can be associated with the measured data set again after transmission. This can comprise integrating a suitable signature in the measured data set or the sub-units, for example a header or trailer. This can also be ensured by targeted actuation or targeted temporal synchronization of the actuation and read-off of the plurality of evaluation units or forwarding units while the measured data set is read off or otherwise. For example, the identifiability may be achieved by a fixed pattern in the data stream that is to be transmitted from the evaluation units to a read-off unit, wherein the sequential arrangement of the measured data sets or partial measured data sets of different evaluation units in the data stream follows this fixed pattern. For example, a time slot—that is to say a time window—or a plurality of time slots may be associated with each evaluation unit, in relation to a start signal that is output to the evaluation units, wherein transmission of a measured data set or the partial measured data sets of a respective evaluation unit is performed in each case within the time slot or slots associated therewith.

A forwarding unit of the number of forwarding units may comprise a digital switching element that is constructed to forward to a receiving unit that is coupled by way of a data line, over a common data output, data that has been received from the forwarding unit by way of at least two separate data inputs. In variant embodiments, the forwarding unit may also have more than two data inputs for receiving measured data sets from the evaluation units of the plurality, and be constructed to output to a receiving unit that is coupled by way of a data line, over a common data output, the data that is received over the more than two separate data inputs.

The forwarding unit may have a buffer memory, which can provide interim storage of a measured data set or partial measured data set that arrives at a data input, before being forwarded. The data that is stored in the buffer memory may correspond in each case to a data packet or a partial measured data set that is to be transmitted, which is then forwarded as a cohesive data block via the forwarding unit.

Preferably, the number of forwarding units is integrated into at least some of the plurality of evaluation units themselves, or is arranged at least near to or between the evaluation units of the plurality, for example on a common support unit. In this way, it is possible to group data lines nearby.

The forwarding unit may for example take the form of a multiplexer. In that case, it is possible for a coupled receiving unit to have a demultiplexer. For data transmission, the forwarding unit and the receiving unit may also take the form of a serializer/deserializer interface (SerDes interface). The forwarding unit and the receiving unit may in that case have suitable SerDes IP chips as the transmitter and receiver. The forwarding unit may for example comprise a network router or network switch that is constructed to direct received data packets to a destination address. Moreover, other variant embodiments are also possible.

Advantageously, with a configuration of this kind of an X-ray module, it is possible to reduce the number of lines required, in that the forwarding unit or units can be used to transmit in each case measured data sets from more than one evaluation unit over a common data line. Advantageously, this also makes it possible to reduce the number of contacts required and, in connection therewith, where applicable a plug size, at least at a read-off unit downstream of the evaluation units or at circuits provided downstream for data processing of the measured data sets from the plurality of evaluation units.

According to a variant embodiment of the X-ray detector module, the one respective forwarding unit of the number of forwarding units is in each case constructed such that it is integrated into an evaluation unit of the plurality of evaluation units. This means that at least one evaluation unit of the plurality of evaluation units has an internal forwarding unit.

In the evaluation unit, which takes the form for example of an ASIC, as well as the switching elements forming the pixel electronics units it is possible for a digital switching element that forms the forwarding element to be constructed.

The evaluation unit may provide within it a data line that, within the evaluation unit, outputs the measured data set to the first data input of the forwarding unit. Moreover, the evaluation unit may in that case have at least one data input that is linked to the second data input of the integrated forwarding unit, with the result that a measured data set received over this can be forwarded to the internal forwarding unit. If the forwarding unit has more than two data inputs, the evaluation unit can also have more than the one correspondingly connected data input. Moreover, the evaluation unit may moreover have a data output that is coupled to the common data output of the internal forwarding unit, with the result that the measured data sets received via the integrated forwarding unit can be forwarded to the receiving unit coupled to the data output of the evaluation unit by way of the data output of the evaluation unit.

Preferably, each of the evaluation units of the plurality may have a forwarding unit, such that the evaluation units of the plurality of evaluation units are of the same construction. This can contribute to cost-efficient provision of the plurality of evaluation units.

Advantageously, as a result of an integrated construction, there is no need for an additional component comprising the forwarding unit, and a construction that is particularly compact with few lines is possible. In particular for the construction of direct-conversion X-ray detectors, it is frequently advantageous if a respective evaluation unit, and with it the pixel electronics units, are connected in the converter unit (sensor pixel) as near as possible to the sensitive volume associated with a pixel electronics unit. This can result in a layout of the evaluation units in which in each case the electronics pixel has the same surface area as a sensor pixel, such that locally a one-to-one association is achieved. If the evaluation unit is constructed using small-scale CMOS technology, however, it is often the case that the pixel electronics units need less surface area than that determined by the sensor. As a result, free space may be left between the pixel structures. This space may be utilized for additional functionality, such as the integration of a forwarding unit, at no additional cost.

Furthermore, a respective forwarding unit may also take the form of a component embodied separately. A respective forwarding unit can thus be provided in addition to the evaluation units of the plurality of evaluation units. Preferably in a configuration of this kind, the forwarding unit is arranged near to the evaluation units coupled thereto. For example, on a common support unit on which the plurality of evaluation units are arranged.

Advantageously, an implementation without any changes to the circuit layout of the evaluation units itself is also possible, and hence also a structure based on any already existing components.

According to a variant embodiment of the X-ray detector module, each of the evaluation units of the plurality of evaluation units has a signal link to a forwarding unit for forwarding a measured data set that is provided by the evaluation unit. Advantageously, data transmission of all the evaluation units of the plurality is grouped together.

According to a variant of the X-ray detector module, the number of forwarding units comprises a plurality of forwarding units, wherein the forwarding units of the number are connected one after the another in the manner of a string of beads, wherein each forwarding unit of the plurality receives measured data sets forwarded at most by one further forwarding unit.

In this variant embodiment, forwarded measured data sets from forwarding units that are upstream in the string can each be forwarded to forwarding units that are downstream in the string.

In this variant, a respective forwarding unit of the plurality can for example comprise only two data inputs. By way of the first data input, it is possible to receive a measured data set from an evaluation unit coupled directly to the data input. The second data input can be coupled in each case to a further forwarding unit and hence receive forwarded measured data sets. The last forwarding unit in the string of forwarding units can then forward the received measured data sets to an evaluation unit.

An arrangement of this kind, linearly one after the other in the manner of a string of beads, may have at its end a forwarding unit that is for example either coupled directly, in each case by way of two data inputs, to a respective evaluation unit for receiving measured data sets. Alternatively, it is also possible for only one data input to be put to use for receiving a measured data set from an evaluation unit directly coupled thereto, and for a second data input to remain unused.

An arrangement of this kind, linearly one after the other in the manner of a string of beads, may advantageously correspond to a particularly simple structure.

However, with an arrangement one after the other, it must be noted that, as the number of measured data sets to be forwarded increases, the data rate for transmission to a downstream forwarding unit or other type of receiving unit increases. Accordingly, care must be taken in the layout and the interfaces and data lines used that they are suitable for transmission of the occurring data rates. In this context, a different construction of data lines and interfaces, depending on the data rate to be expected, may also be taken into account. Preferably, however, the same connection set-up is used.

As an alternative to a linear connection set-up in the manner of a string of beads, it is also possible to lay out the forwarding units in tree form—that is to say branching—wherein at least some of the forwarding units are coupled in a signal-carrying manner, by way of two separate data inputs of these some of the forwarding units, to at least two further forwarding units of the plurality of forwarding units.

In this variant, a respective forwarding unit may preferably have at least three data inputs. A measured data set from an evaluation unit that is directly coupled to a first data input may be received over a first data input, and forwarded measured data sets from the two further forwarding units may be received over a second and a third data input.

In this variant embodiment, overall fewer forwarding units are required than in a linear connection set-up. Likewise, the data rate for transmission may be lower, at least over some of the data lines to be connected, than with a purely linear connection set-up of the forwarding units.

According to a variant embodiment of the X-ray detector module, a respective forwarding unit comprises a multiplexer. A construction of a forwarding unit as a multiplexer may correspond to a particularly simple implementation. In particular, a multiplexer may be integrated into the circuit layout of an evaluation unit in a simple manner.

A multiplexer may take the form of a digital logic gate that is constructed to select one from a number of input signals and to connect it through to the output of the multiplexer. Consequently, a multiplexer can receive a plurality of data streams over separate data inputs and output them to a common data line over a common data output. Via a demultiplexer formed in a receiving unit, the transmitted data streams can be separated again. As well as a plurality of inputs and one output, a multiplexer may have one or more control signals that enable determination of which input is selected and connected through to the output. A multiplexer can thus be used as a data selector for the data transmission with time-dependent control—that is to say for selection of the data inputs for forwarding to the data output with time-dependent control. The multiplexer may be constructed to switch cyclically between the data inputs such that data arriving at a data input, or where appropriate data stored temporarily in a buffer memory, can respectively be forwarded sequentially to the data output and transmitted to the receiving unit.

For transmission between a respective forwarding unit and a receiving unit, in variant embodiments it is possible to use for example a simple data line, for example a CMOS data line. However, it should be noted that the data rate that this can transmit reliably may be limited. In particular, a simple line of this kind may not be very suitable for transmission at a data rate of more than 30 Mbit/s or 40 Mbit/s. For higher data rates, a differential signal transmission, for example using LVDS lines, may be used for data transmission of the measured data sets between a respective forwarding unit and the receiving unit coupled thereto. Low voltage differential signaling (LVDS) is an interface standard for high-speed data transmission, based on a differential signal transmission using a complementary pair of lines. An LVDS line may be less susceptible to faults. In this way, data rates of several hundred Mbit/s can be achieved.

According to a further variant embodiment of the X-ray detector module, a serializer/deserializer interface (SerDes) is used for data transmission between a respective forwarding unit and the receiving unit coupled thereto.

A SerDes interface is substantially a serial transmitter/receiver device that converts data received in parallel on the transmitter side into a serial data stream, and can convert the serial data back into parallel data streams on the receiver side. For this purpose, the forwarding unit can have a serializer and the receiving unit can have a deserializer respectively. A Ser/Des chip used in the forwarding unit or receiving unit may in particular furthermore have additional functional units for the clock generation for the purpose of data transmission on the serializer side or functional units for clock recovery on the deserializer side. A so-called embedded-clock SerDes interface may be used, with which the required clock signal is embedded in the serial data transmission in the serializer, and the receiving clock is recovered in the deserializer. As an alternative, the clock signal may also be transmitted separately. Preferably, a differential line pair, that is to say substantially an LVDS line, can be used for data transmission. A SerDes method comprising an 8b/10b line coding can be used to enable clock recovery and equalization and provide rudimentary protection against faults. If an 8b/10b SerDes method is used, data transmission for example via optical fiber may moreover be possible.

Using data transmission via a SerDes interface, transmissible data rates of up to several Gbps, for example 5 Gbps, can be achieved. If for example electrical or optical 10 Gbit Ethernet interfaces are used, it is possible to achieve even higher data rates with commercially available components.

According to a variant embodiment of the X-ray detector module, a respective forwarding unit comprises a network router or network switch.

The plurality of evaluation units, the one or more forwarding units and the one or more receiving units can form a network, wherein for the purpose of connection or communication between the units in the network a network protocol can be used for transmission of the measured data sets in the form of data packets to be transmitted. Here, a measured data set can be transmitted as a data packet or indeed in multiple parts in the form of a plurality of data packets. Each evaluation unit and/or forwarding unit and/or receiving unit in the network can have a network address. The network router or switch can in that case be constructed to direct data packets that are received over its data inputs to a destination address by way of the common data output. The destination address may be for example a read-off unit. The data inputs and outputs may for example comprise a variant on the Ethernet standard, a BNC connector, or a connector for an optical fiber.

The inventor has realized that data transmission or data forwarding based on forwarding units that can be used as a network switch or network router and network protocols, for example TCP/IP and Ethernet. In this way, instead of data transmission sections developed inhouse, it is advantageously possible to use commercially available components and interfaces. Advantageously, the complexity of cabling and the susceptibility to faults can be reduced. Advantageously, it is possible to resort to available data network tools for fault location.

It is possible for communication to take place for example in only one direction—so-called simplex. The data may flow in both directions alternately—so-called half duplex. The data may flow in both directions at the same time—so-called full duplex. With synchronous data transmission, communication can be synchronized by way of a clock signal. Because a network of this kind may also be constructed for communication toward the evaluation units using the same data lines, advantageously control data for the evaluation units may also be transmitted over the network to the evaluation units, and hence the evaluation units may be controlled without the need to provide additional lines.

According to one embodiment of the invention, for the purpose of communication between an evaluation unit or forwarding unit and a receiving unit, a network protocol may be used. The network protocol is a communication protocol for exchanging measured data sets between an evaluation unit and a forwarding unit or a forwarding unit and a receiving unit. During communication, different protocols taking on different tasks, for example the Internet protocol family, may be used together. The protocols can form a protocol stack based on the ISO OSI reference model or DoD layer model. The tasks of a protocol may comprise the construction of secure and reliable connection between the units involved in communication, the reliable delivery of packets, repeated sending of packets that have not arrived, delivery of data packets to the desired recipient or recipients, ensuring fault-free transmission, joining together arriving data packets in the correct order, the prevention of reading by unauthorized third parties, and/or the prevention of tampering by unauthorized third parties.

The structure of a data packet that is described in a protocol contains information on the packet that is important for data exchange, such as sender and recipient, type of packet, packet size, in the case of multiple-part transmissions the serial number and the total number of packets, and a checksum for tracking fault-free transmission. This information can be placed before the useful data as a header, or be attached thereto as a trailer. The protocol may have end-to-end control of transmission. For example, as the protocol in the transport layer the transmission control protocol (TCP) monitors complete delivery of the data packets, and moreover the data packets are put in the right order.

For example, for the purpose of communication an Internet protocol is used. Internet protocols that may be used are for example TCP, SCTP, TLS or UDP. Preferably, TCP/IP may be used. In the Internet or network layer, IP may for example be used. In the network access layer, it is possible to use for example MAC or Ethernet, for example 1 Gbps Ethernet or 10 Gbps/s Ethernet. Further, the protocol stack comprises a corresponding physical layer.

A measured data set from an evaluation unit can be provided directly in the evaluation unit with a header that identifies the measurement interval and the evaluation unit. This allows the data to be sent as TCP/IP packets over the network and one or more forwarding units, ultimately to reach a read-off unit.

The network infrastructure that is for data transmission can also be used for synchronizing the evaluation units. For example, network-based protocols such as IEEE 1588 over Ethernet or TCP/IP can be used. In that case, in addition to the evaluation unit data that is in particular measured or read off, data packets can moreover have an item of time information. Each evaluation unit can have a real-time clock that can be precisely synchronized to within fractions of a microsecond with the real-time clocks of the other evaluation units and a central reference real-time clock of a timing element. Commands for the start of measurement periods are transmitted to all evaluation units in advance indicating a desired start time, the predetermined point in time. Advantageously, commercially available components may be used for the synchronization, for example on the basis of IEEE 1588, also called the precision time protocol (PTP). Advantageously, the network cabling that is for data transmission may additionally be used for synchronization. Advantageously, the complexity of cabling and the susceptibility to faults may be reduced.

Furthermore, at least one embodiment of the invention relates to an evaluation unit, comprising an integrated forwarding unit, for use in an X-ray detector module according to one of the embodiments described.

The description that has been given in respect of the X-ray detector module, and the advantages of the X-ray detector module that have been described above, can accordingly also be transferred to the evaluation unit according to embodiments of the invention.

Furthermore, at least one embodiment of the invention relates to a medical imaging apparatus, comprising a detection unit with at least one X-ray detector module according to an embodiment of the invention and, arranged opposite this, an X-ray source that is constructed to expose the detection unit, and hence the converter unit coupled to the first plurality of evaluation units of the X-ray detector module, to X-ray radiation.

The medical imaging apparatus may also comprise more than one X-ray detector module.

For receiving the X-ray image data set, it is possible to place the object for imaging between the X-ray source and the detection unit and to irradiate it via the X-ray source.

In particular, the medical imaging apparatus may take the form of a computed tomography system. The medical imaging apparatus may also take the form of a SPECT or PET system. However, it may also take the form for example of a C-frame X-ray device and/or Dyna-CT or another form.

All the variant embodiments that are described above in the context of the X-ray detector module according to embodiments of the invention may also be embodied accordingly in the medical imaging apparatus. The description that has been given in respect of the X-ray detector module, and the advantages of the X-ray detector module that have been described above, can accordingly also be transferred to the medical imaging apparatus according to embodiments of the invention.

Furthermore, at least one embodiment of the invention relates to a method for operating an X-ray detector module according to one of the variants described above. The method has the steps of exposure, recording and forwarding.

During the exposure, the converter unit that is coupled to the plurality of evaluation units is exposed to X-ray radiation via an X-ray source.

In the recording, a measured data set is recorded for each evaluation unit, based on the incident X-ray radiation.

In the forwarding measured of data sets by a forwarding unit of the number of forwarding units, either: a measured data set from a first evaluation unit of the plurality of evaluation units is received by way of a first data input of the forwarding unit of the number, and a measured data set from a second evaluation unit, different therefrom, of the plurality is received by way of a second data input, and the measured data sets that are received by way of the first data input and second data input are forwarded to a receiving unit via the forwarding unit over a common data output.

Or: in the forwarding, a measured data set from a first evaluation unit of the plurality is received by way of a first data input of the forwarding unit, and a forwarded measured data set from a further forwarding unit of the number of forwarding units is received by way of a second data input, and the measured data sets that are received by way of the first data input and second data input are forwarded to a receiving unit via the forwarding unit over a common data output A.

Within the context of embodiments of the invention, it is moreover possible for features that are described in relation to different embodiments of the invention and/or different claim categories (method, use, apparatus, system, arrangement, etc.) to be combined to give further embodiments of the invention. For example, a claim that relates to an apparatus may also be developed using features that are described or claimed in the context of a method, and vice versa. Here, functional features of a method may be formed by correspondingly formed components relating to an item. As well as the embodiments of the invention that are explicitly described in this application, numerous further embodiments of the invention are conceivable which those skilled in the art may arrive at without departing from the scope of the invention that is defined by the claims.

The use of the indefinite articles "a" and "an" does not rule out the possibility that the feature concerned may also be present a plurality of times. The use of the expression "have" does not rule out the possibility that the terms linked by the expression "have" may be identical. For example, the medical imaging device has the medical imaging device. The use of the expression "unit" does not rule out the possibility that the item to which the expression "unit" relates may have a plurality of components that are spatially separated from one another.

FIG. 1 shows an example embodiment of a medical imaging device 32 with a detection unit 36, which comprises at least one X-ray detector module 100 according to the invention, and an X-ray source 37 opposite the detection unit 36. The X-ray source is constructed to expose the detection unit 36, and hence a converter unit that has a signal link to a plurality of evaluation units 1 of the at least one X-ray detector module 100, to X-ray radiation. The medical imaging device 32 that is shown takes the form in particular of a computed tomography system. The computed tomography system contains a gantry 33 with a rotor 35. The rotor 35 comprises an X-ray source 37 and the detection unit 36. The rotor 35 is rotatable about the axis of rotation 43. The object undergoing investigation 39, in this case a patient, is mounted on the patient table 41 and can be moved through the gantry 33 along the axis of rotation 43. For the purpose of controlling the computed tomography system and/or calculating sectional or volume images of the object, a processing unit 700 is used. An input facility 47 and an output apparatus 49 are connected to the processing unit 700.

A detection unit 36 of a medical imaging device 32 of this kind, in the form of a computed tomography system, typically comprises a multiplicity of X-ray detector modules 100, which are arranged next to one another in the direction of rotation and/or one behind the other along the axis of rotation 43, with the result that overall a detection surface area of advantageous size is formed by the X-ray detector modules 100. In other variant embodiments of a medical device, the detection unit may also take a different form and comprise for example only one X-ray detector module 100.

For the purpose of transmitting data between the detection unit 36 and the processing unit 45 in a medical imaging device, it is possible for a transmission unit 500 to be formed, for example in the computed tomography system shown here a slip ring transmission system. The slip ring transmission system may comprise capacitive transmission, radio transmission or optical transmission. Advantageously, the transmission may be performed wirelessly. The transmission unit 500 is connected by way of connections to the processing unit 700.

Figure 2:
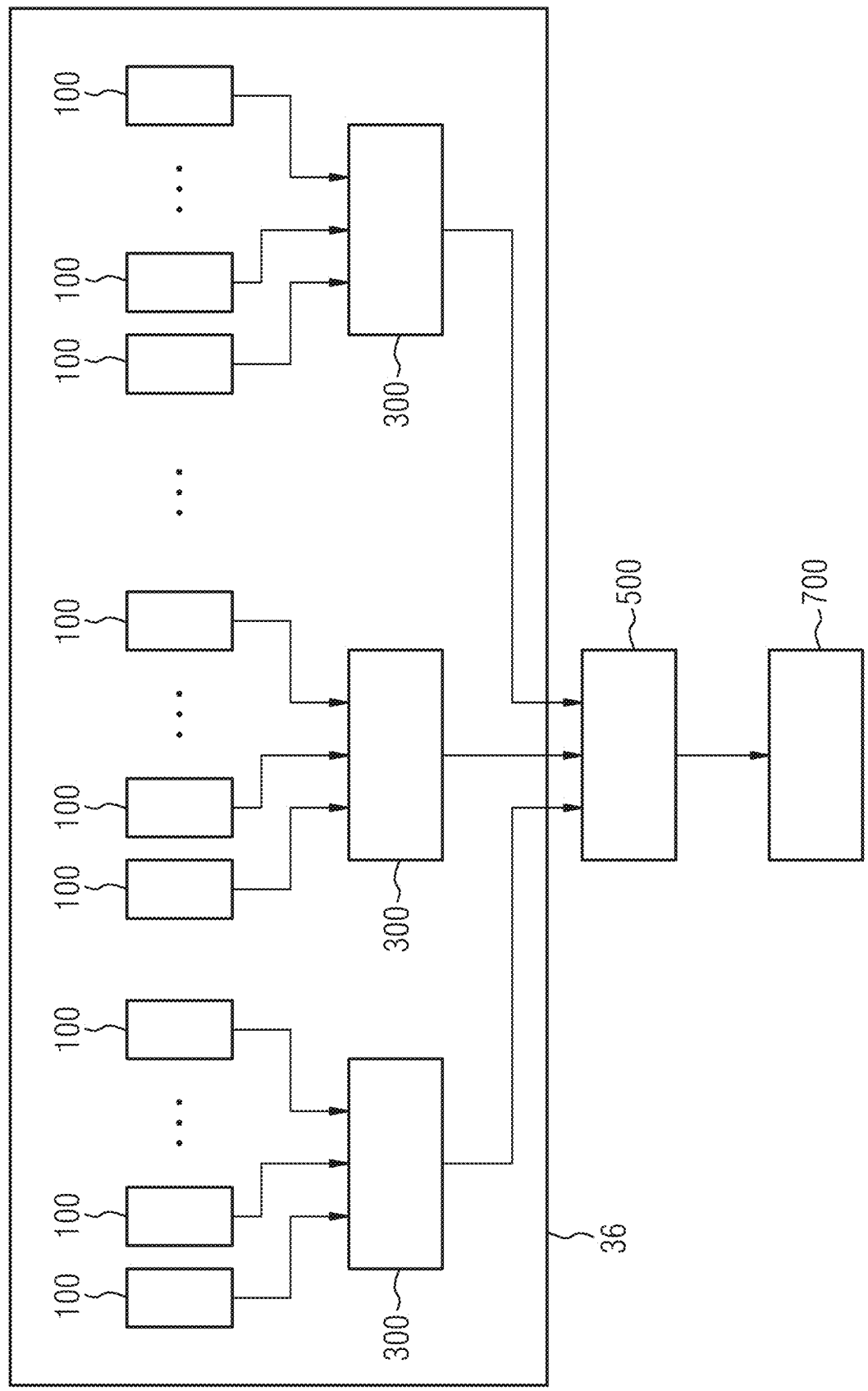
FIG. 2 shows an illustration of an example construction of a detection unit of a medical imaging device, with a plurality of X-ray detector modules.

FIG. 2 shows a schematic illustration of an example structure of a detection unit 36 with a plurality of X-ray detector modules 100 as can be used in FIG. 1. In addition, embodiments deviating from this are also possible. The arrows shown illustrate in particular only a flow of information from the X-ray detector modules 100 to a processing unit 700. The arrows do not give any indication of the number or form taken by any lines provided for this purpose. Moreover, the flow of information is shown only in one direction, from the X-ray detector modules 100 and toward a processing unit 700. Consequently, this symbolizes in particular the flow of information of the measured data sets from the evaluation units 1 of the X-ray detector modules 100, when the measured data sets are read off, to a processing unit 700, which may be constructed for image generation based on the read-off measured data sets. For the purpose of actuating and controlling the components shown, there may also be a flow of information (not illustrated here) of control signals in the other direction, toward the X-ray detector modules 100. The control signals may comprise a start signal for read-off. They may also comprise a clock signal for transmission of the measured data sets, or a synchronization signal. For this purpose, in variant embodiments the same line infrastructure can be used as that provided for read-off. However, it is also possible in particular to provide control signal lines that are separate therefrom and that transmit the control signals to an X-ray detector module 100 and to the evaluation units 1 of the X-ray detector module 100.

In this example, the detection unit comprises a plurality of X-ray detector modules 100. In the example shown, in each case a plurality of X-ray detector modules 100 is furthermore associated with a common data transmission intermediate unit 300, from which the data of the X-ray detector modules 100 associated therewith is forwarded by way of the transmission unit 500 to the processing unit 700. A data transmission intermediate unit 300 lying in between may serve for example to collect and compress the data to be transmitted from the X-ray detector modules 100 associated therewith.

Figure 3:
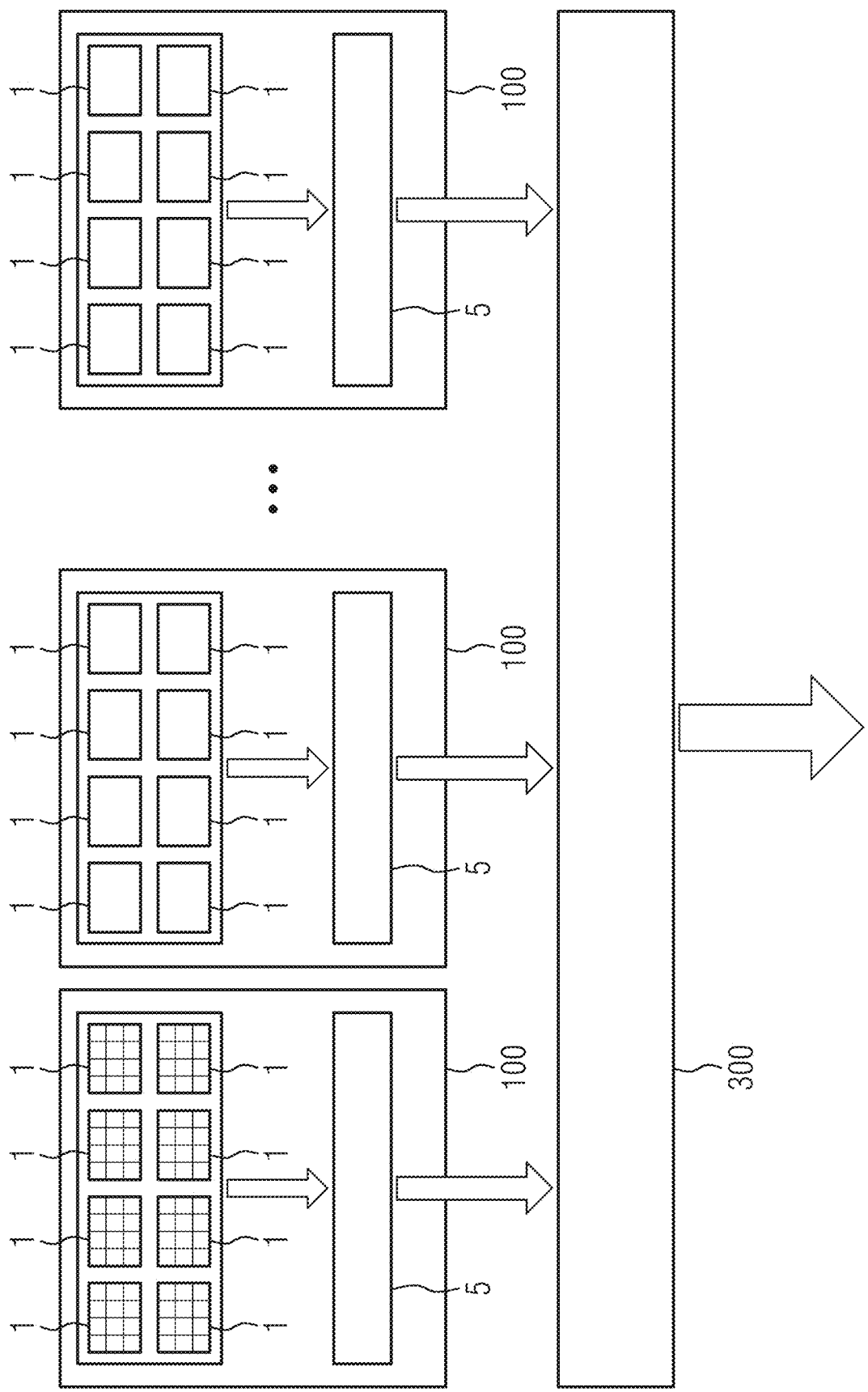
FIG. 3 shows a detail of the example construction in FIG. 2.

FIG. 3 shows a detail of the example structure illustrated in FIG. 2, in a schematic illustration comprising a data transmission intermediate unit 300 and X-ray detector modules 100 associated therewith. In the example shown, each X-ray detector module 100 comprises a read-off unit 5 and a plurality 3 of evaluation units 1. The plurality 3 of evaluation units 1 may for example be associated in each case with a cohesive common converter unit, or arranged together on a support unit.

In the example shown, the plurality of evaluation units 1 comprises six evaluation units 1. The plurality may also comprise other numbers of evaluation units 1. Likewise, there may be several evaluation units 5 for each X-ray detector module 100, with which one or more pluralities of evaluation units 1 is respectively associated.

The read-off unit 5 is constructed to receive the measured data of the evaluation units 1 associated therewith and to forward it to the data transmission intermediate unit 300. The read-off unit 5 may for example take the form of a multiple-layer read-off board. The read-off unit 5 may have circuits that perform interim further processing of the received measured data sets. This may for example comprise compression of the measured data for simplified data transmission, or indeed correction of the measured data. The read-off unit 5 may for example comprise one or more programmable gate arrays, FPGAs, which is/are configured to receive measured data sets from the plurality 3 of evaluation units 1 and/or to perform interim further processing of the measured data sets. In variant embodiments, the data transmission intermediate unit 300 may also comprise the read-off units 5.

As well as receiving and forwarding measured data sets from the evaluation units 1, the read-off units 5 may also be constructed for generating and passing on control signals to the evaluation units 1, such that actuating and controlling of the evaluation units 1 is enabled.

The evaluation units 1 of the plurality 3 of evaluation units 1 of an X-ray detector module 100 may in particular take the form of an application-specific integrated circuit (ASIC). Each evaluation unit 1 is coupled to a converter unit, which is constructed to convert incident X-ray radiation into electrical signals. Here, a plurality of evaluation units 1 may be associated with one converter unit. The coupled converter unit may take the form of a direct-conversion or indeed an indirect-conversion converter unit.

Each evaluation unit 1 of the plurality of evaluation units 1 has a multiplicity of pixel electronics units, for processing the electrical signals from the converter unit that is associated therewith, pixel by pixel and hence in a spatially resolved manner. This is indicated schematically on the left-hand side of FIG. 3 by an example subdividing of the evaluation units 1 of the X-ray detector module 100 that are illustrated here, wherein a measured data set can be provided on the basis of the processed electrical signals of the multiplicity of pixel electronics units of each evaluation unit 1 of the plurality of evaluation units 1. On the basis of the measured data sets of the evaluation units 1, it is possible to reconstruct an X-ray image data set using the processing unit 700.

Besides the construction explained here by way of example, there are of course also other possibilities for a construction of the detection unit 36 or the X-ray detector module 100. Furthermore, further components of a detection unit 36 may be included, or be arranged between a detection unit 36 and a processing unit 700.

For data transmission from the evaluation units 1 of the plurality of evaluation units 1 to a read-off unit 5, corresponding data lines that can transmit the measured data sets of the evaluation units 1 to the read-off unit have to be provided.

According to an embodiment of the invention, in this context a number of forwarding units 7 is provided, wherein a forwarding unit 7 of the number of forwarding units either has at least a first data input E1 for receiving a measured data set from a first evaluation unit 1 of the plurality and a second data input E2 for receiving a measured data set from a second evaluation unit 1, different from the first, of the plurality, or it has at least a first data input E1 for receiving a measured data set from a first evaluation unit 1 of the plurality of evaluation units 1 and a second data input E2 for receiving at least one forwarded measured data set from a further forwarding unit 7 of the number of forwarding units 7.

Each forwarding unit 7 of the number is furthermore constructed to forward the measured data sets that are received by way of the first data input E1 and second data input E2 to a coupled receiving unit 7, 5 over a common data output A. The receiving unit can in this case be a further forwarding unit 7 of the number of forwarding units, or indeed for example the read-off unit 5. A respective receiving unit 5, 7 is connected by way of a data line and the common data output to the coupled forwarding unit 7 for the purpose of data transmission.

Using the forwarding unit 7, common data transmission of measured data sets from different evaluation units 1 of the plurality of evaluation units 1 over a common data line can advantageously be achieved. Preferably, the number of forwarding units 7 is integrated into at least some of the plurality of evaluation units themselves, or is at least arranged near to or between the evaluation units 1 of the plurality of evaluation units 1, for example on a common support unit. In this way, it is advantageously possible to provide local grouping of data transmission.

A forwarding unit 7 of the number of forwarding units 7 may for example as a multiplexer having at least two separate data inputs E1 and E2 and a common data output A. The receiving unit 5, 7 may then have a demultiplexer. The forwarding unit 7 and the receiving unit 5, 7 may take the form of a serializer/deserializer interface (SerDes interface). The forwarding unit 5 may then have a corresponding SerDes IP chip as the transmitter, with the result that the forwarding unit 5 can receive measured data sets over at least two separate data inputs E1, E2 and can send them to the receiving unit 5, 7 over a common data output A. The receiving unit 5, 7 may have a corresponding SerDes IP chip as receiver, which then in turn is constructed to separate data received over a common data line. The SerDes chips may in particular comprise further functional units that have for clock generation on the serializer side, and functional units for clock recovery on the deserializer side. The forwarding unit 5 may for example also comprise a network router or network switch that is constructed to forward data packets that are received over two separate data inputs E1, E2 to a destination address over a common data output. The receiving unit 5, 7 may be constructed to receive and process the data packets, or to forward them again to a destination address.

The data lines for transmitting the measured data sets may be constructed depending on the data rate to be expected and the interface used. The data lines may be formed for example as a simple CMOS line, an LVDS line, an Ethernet line or indeed as an optical fiber. Preferably, all the forwarding units 7 are constructed in the same way for the sake of cost-efficient construction, so the same interfaces and lines are used for all the forwarding units 7.

Advantageously, with a construction of this kind of an X-ray module, it is possible to reduce the number of lines required from the evaluation units 1 of the plurality of evaluation units 1, in that, via the forwarding unit or units 7, measured data sets from more than one evaluation unit 1 may each be transmitted over a common data line.

Figure 4:
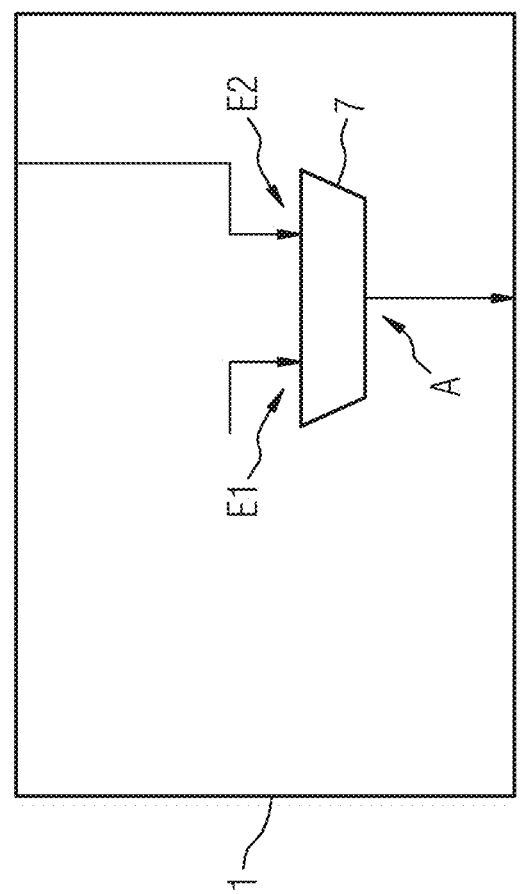
FIG. 4 shows an example variant embodiment of a forwarding unit, in conjunction with an evaluation unit.

FIG. 4 shows by way of example a variant embodiment of a forwarding unit 7, in conjunction with an evaluation unit 1.

According to a variant embodiment, the forwarding unit 7 shown here is integrated into an evaluation unit 1 of the plurality of evaluation units 1. Implemented in the evaluation unit 1, as well as the switching elements that form the pixel electronics units, is a digital element that forms the forwarding unit 7. The forwarding unit 7 in this variant has only two data inputs E1 and E2. The evaluation unit 1 has within it a data line to the first data input E1 of the forwarding unit 7, with the result that the measured data set from the evaluation unit 1 shown can itself be received by the forwarding unit 7. Moreover, the evaluation unit 1 has a data input that is coupled to the second data input E2 of the forwarding unit 7, with the result that by way of the data input of the evaluation unit 1 a further evaluation unit 1 of the plurality of evaluation units 1, or a further forwarding unit 7 of the number of forwarding units 7, can be coupled by way of a data line. The evaluation unit 1 moreover has a data output that is coupled to the common data output A of the forwarding unit 7, with the result that over this the measured data sets that are received from the forwarding unit 7 can be forwarded to a receiving unit 5, 7 that is coupled thereto by way of a data line.

Figure 5:
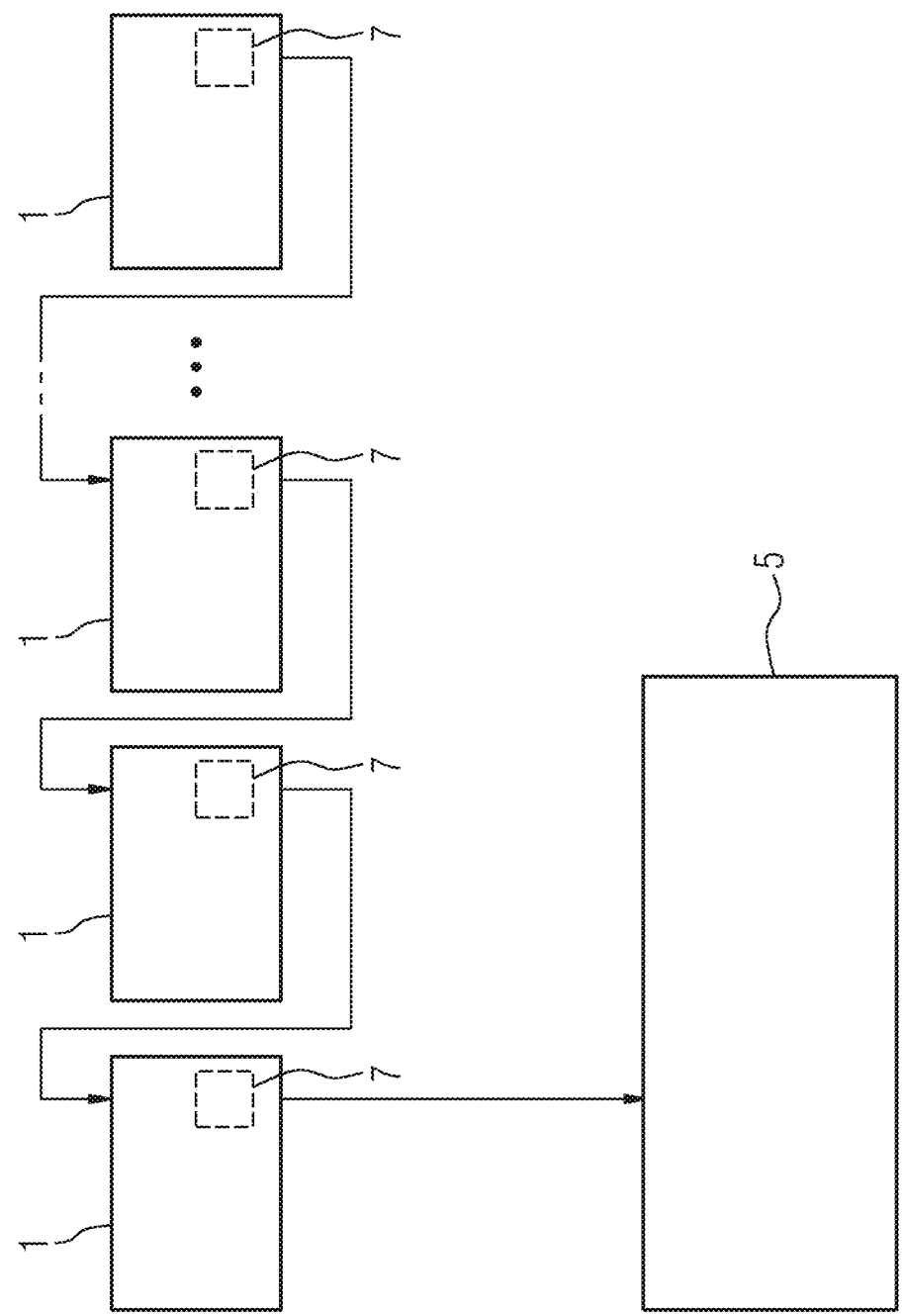
FIG. 5 shows a variant embodiment of a connection set-up of a plurality of evaluation units of an X-ray detector module.

FIG. 5 shows a variant embodiment of a connection set-up of a plurality of evaluation units 1 of an X-ray detector module 100 having a plurality of evaluation units 1. Each of the evaluation units 1 of the plurality of evaluation units 1 has an integrated forwarding unit, as shown by way of example in FIG. 4. Each of the evaluation units 1 is coupled, by way of the data output described in conjunction with FIG. 4, to a data input of a further evaluation unit 1 of the plurality of evaluation units 1 by way of a data line. In this way, the evaluation units 1 and likewise the forwarding units 7 are constructed such that they are connected one after the other in the manner of a string of beads. The forwarding units 7 of the number of forwarding units 7 are connected one after the other in the manner of a string of beads, wherein each forwarding unit 7 of the plurality receives forwarded measured data sets at most from one further forwarding unit 7, namely the forwarding unit 7 that is upstream thereof in the string.

In this variant embodiment, forwarded measured data sets from forwarding units 7 that are upstream in the string may be forwarded to forwarding units 7 that are downstream in the string, in each case by way of a direct data line.

The last forwarding unit 7 in the string of forwarding units 7 then forwards the received measured data sets to the read-off unit 5.

In the example shown, the first evaluation unit 1 in the string also has a forwarding unit 7. In this case, however, a data input E2 of the forwarding unit 7 is put to use. The fact that all the evaluation units 1 of a detector apparatus 36 have the same construction may in particular correspond to simple, low-cost implementation, since there is no need for different circuit layouts for evaluation units to be implemented.

Figure 6:
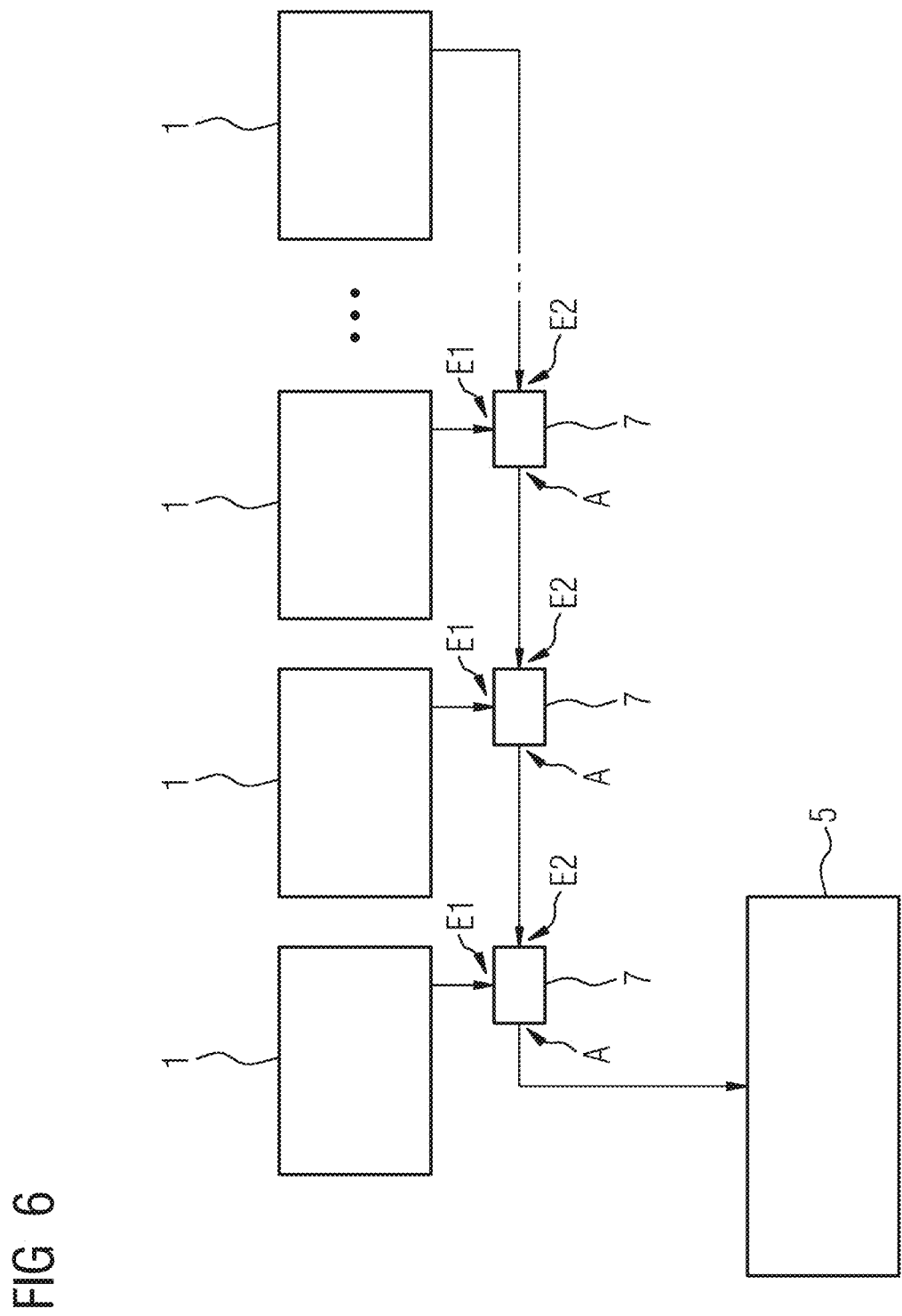
FIG. 6 shows a second variant embodiment of a connection set-up of a plurality of evaluation units of an X-ray detector module.

FIG. 6 shows an alternative embodiment of a connection set-up of evaluation units 1. This example likewise comprises connecting the number of forwarding units 7 in the manner of a string of beads, and thus linearly one after the other. In this case, however, the forwarding units 7 take the form of a separate component. This means that the forwarding units are not integrated in the circuit layout of the evaluation units 1. The forwarding units 7 may be arranged for example as separate circuits between the evaluation units 1 on a common support unit. In that case, the evaluation units 1 each have a data output that is coupled to a forwarding unit 7 for the purpose of transmitting the measured data set that it provides.

Figure 7:
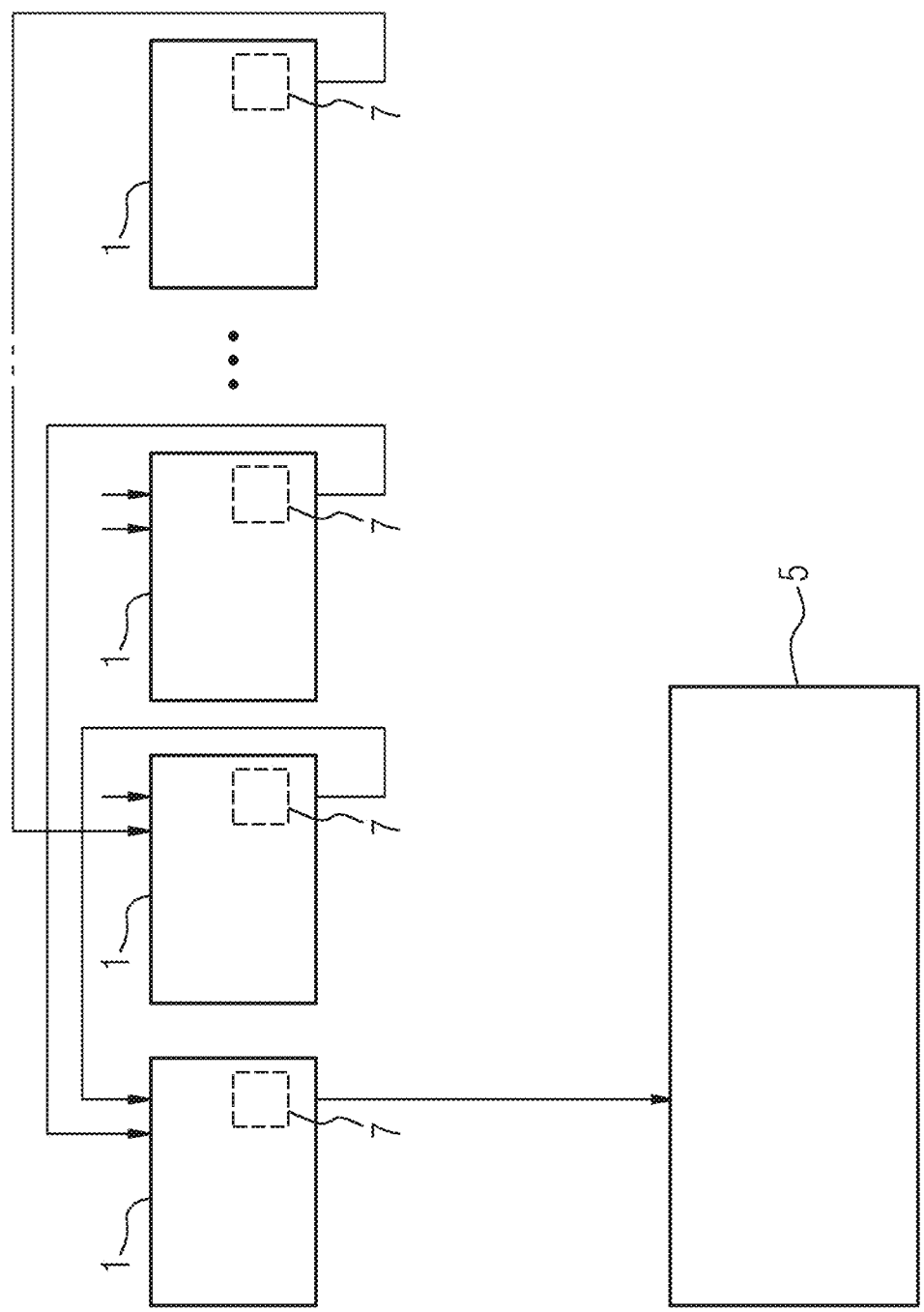
FIG. 7 shows a third variant embodiment of a connection set-up of a plurality of evaluation units of an X-ray detector module.

FIG. 7 shows a further variant embodiment of a connection set-up of the evaluation units 1 of the plurality of evaluation units 1 of an X-ray detector module 100. Here, the forwarding units 7 are connected in a tree-like set-up, wherein at least some of the forwarding units 7 are coupled in a signal-carrying manner by way of two data inputs embodied separately, E2, E3, of the forwarding units 7 to at least two further forwarding units 7 of the plurality of forwarding units 7. The forwarding units 7 are integrated into the evaluation units 1.

Figure 8:
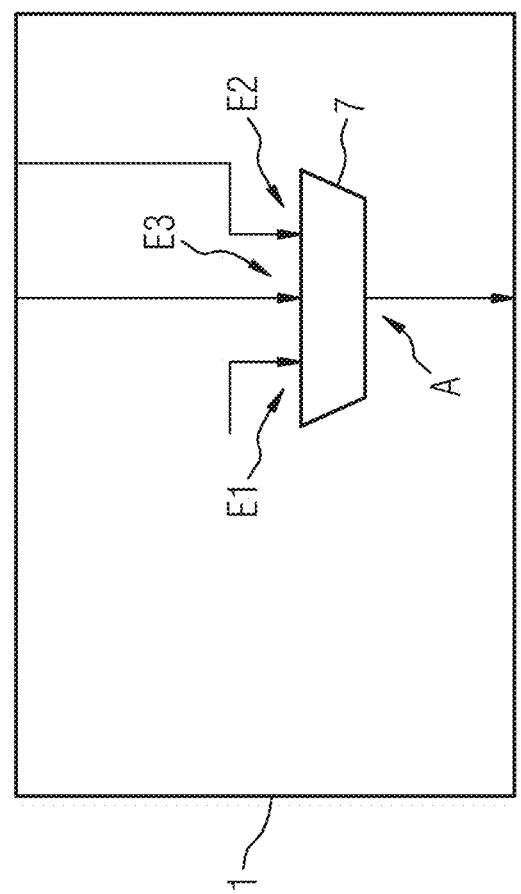
FIG. 8 shows an example second variant embodiment of a forwarding unit, in conjunction with an evaluation unit.

A forwarding unit 7 is illustrated by way of example in FIG. 8 in connection with an evaluation unit 1 from FIG. 7. The forwarding unit 7 has three data inputs E1, E2 and E3. As well as the internal data input E1 for receiving the measured data set from the shown evaluation unit 1 itself, it is possible to receive further measured data sets over the two data inputs E2 and E3, which are linked to a corresponding data input of the evaluation unit 1. The measured data sets that are received over the data inputs E1, E2, E3 can be forwarded over a common data line by way of the common data output A.

Likewise, a tree-like connection set-up as in FIG. 7 would also be possible using forwarding units 7 embodied separately.

Also conceivable are connection set-ups having forwarding units 7 that have more than three data inputs, wherein in each case either measured data sets from evaluation units 1 coupled thereto, or forwarded measured data sets from forwarding units 7 coupled thereto are received over the data inputs.

Figure 9:
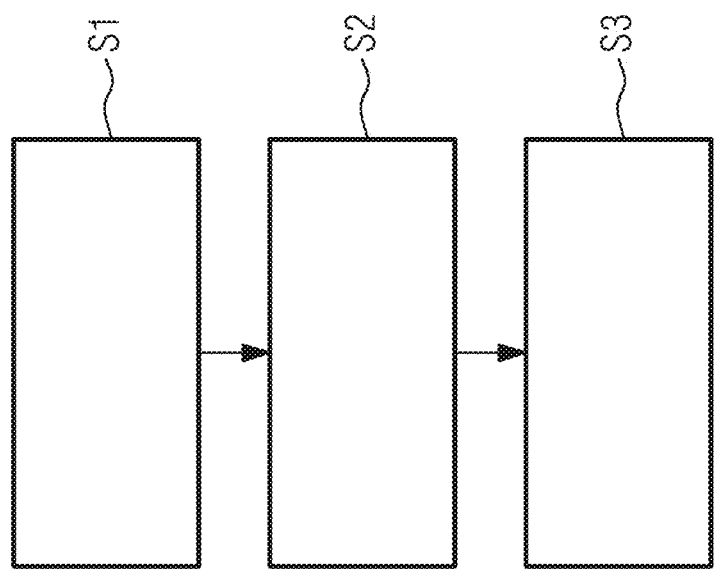
FIG. 9 shows a schematic illustration of a method for operating an X-ray detector module.

FIG. 9 shows a schematic method sequence of a method for operating an X-ray detector module 100 according to an embodiment of the invention.

In the exposure step S1, the converter unit that is coupled to the plurality of evaluation units 1 of the X-ray detector module is exposed to X-ray radiation via an X-ray source 37.

The electrical signal that is generated in the converter unit by the incident X-ray radiation can be forwarded by way of electrically conductive connections to a respective evaluation unit 1, which is coupled to the converter unit, and fed to the pixel electronics units for the purpose of processing the electrical signals.

In the recording step S2, a measured data set is recorded for each evaluation unit 1, based on the incident X-ray radiation. Here, the measured data set is based on the electrical signals that are processed by the multiplicity of pixel electronics units of a respective evaluation unit 1. In each case, one measured data set can be provided by each evaluation unit 1 of the plurality of evaluation units 1 of the X-ray detector module 100.

In the step S3 of forwarding measured data sets by a forwarding unit 7 of the number of forwarding units 7, either: a measured data set from a first evaluation unit 1 of the plurality of evaluation units 1 is received by way of a first data input E1 of the forwarding unit 7 of the number, and a measured data set from a second evaluation unit 1, different therefrom, of the plurality is received by way of a second data input E2, and the measured data sets that are received by way of the first data input E1 and second data input E2 are forwarded to a receiving unit 7, 5 via the forwarding unit 7 over a common data output A.

Or: in the step S3 of forwarding measured data sets, a measured data set from a first evaluation unit of the plurality is received by way of a first data input E1 of the forwarding unit 7, and a forwarded measured data set from a further forwarding unit 7 of the number of forwarding units 7 is received by way of a second data input D2, and the measured data sets that are received by way of the first data input E1 and second data input E2 are forwarded to a receiving unit 7, 5 via the forwarding unit 7 over a common data output A.

For example, a start signal is transmitted to each evaluation unit 1 of an X-ray detector module 100, for the start of a read-off procedure. Moreover, there may be associated with each evaluation unit 1, relative to the start signal, a time slot within which data from the evaluation unit 1 is transmitted. Within the time slot associated therewith, the measured data set or in each case part of a measured data set from an evaluation unit 1 is forwarded to the read-off unit 5 by way of the forwarding unit or units 7. A temporal pattern in the data stream can make the measured data sets or parts of measured data sets identifiable.

As an alternative, data transmission can be performed for example on the basis of a network protocol, wherein the network protocol serves as a communication protocol for the exchange of data between the evaluation units 1, the forwarding units 7 and the read-off unit 5, and can ensure that the measured data sets or parts of measured data sets from an evaluation unit 1 are identifiable.

Of course, the embodiments of the method according to the invention and the imaging apparatus according to the invention described here should be understood as being example. Therefore, individual embodiments may be expanded by features of other embodiments. In particular, the sequence of the method steps of the method according to the invention should be understood as being example. The individual steps can also be performed in a different order or overlap partially or completely in terms of time.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An X-ray detector module, comprising
    at least one converter, constructed to convert incident X-ray radiation into electrical signals;
    a plurality of evaluation circuits, coupled to the at least one converter, each respective evaluation circuit of the plurality of evaluation circuits including a respective multiplicity of pixel electronics to process the electrical signals from the at least one converter pixel by pixel, and based on processed electrical signals of the multiplicity of pixel electronics from each evaluation circuit of the plurality of evaluation circuits, each respective evaluation circuit of the plurality of evaluation circuits being configured to provide a respective measured data set; and
    a number of forwarding circuits, a forwarding circuit of the number of forwarding circuits, including at least a first data input to receive a first measured data set from a first evaluation circuit of the plurality of evaluation circuits and at least a second data input to receive at least one forwarded measured data set from a further forwarding circuit of the number of forwarding circuits, and
    each respective forwarding circuit of the number of forwarding circuits being constructed to forward measured data sets received via the first data input and second data input to a coupled receiving circuit over a common data output.

2. The X-ray detector module of claim 1, wherein each of the evaluation circuits of the plurality of evaluation circuits is coupled in a signal-carrying manner to at least one forwarding circuit for forwarding the respective measured data set provided by the evaluation circuit.

3. The X-ray detector module of claim 1, wherein the number of forwarding circuits includes a plurality of forwarding circuits, wherein forwarding circuits of the plurality of forwarding circuits are connected one after another in a manner of a string of beads, wherein a forwarding circuit of the plurality of forwarding circuits receives measured data sets forwarded at most from one further forwarding circuit.

4. The X-ray detector module of claim 1, wherein the number of forwarding circuits includes a plurality of forwarding circuits, connected in a tree-like set-up, wherein at least some of the plurality of forwarding circuits are coupled in a signal-carrying manner, by way of two separate data inputs of the at least some of the forwarding circuits, to at least two further forwarding circuits of the plurality of forwarding circuits.

5. The X-ray detector module of claim 1, wherein at least one of the number of forwarding circuits includes a multiplexer.

6. The X-ray detector module of claim 1, wherein a serializer/deserializer interface is used for data transmission between a respective forwarding circuit of the number of forwarding circuits and the coupled respective receiving circuit.

7. The X-ray detector module of claim 1, wherein an LVDS line is used for data transmission of the measured data sets between a respective forwarding circuit of the number of forwarding circuits and the coupled respective receiving circuit.

8. The X-ray detector module of claim 1, wherein a respective forwarding circuit of the number of forwarding circuits comprises a network router or a network switch.

9. The X-ray detector module of claim 8, wherein for data transmission of the measured data sets between a respective forwarding circuit of the number of forwarding circuits and the receiving circuit coupled thereto, a network protocol is used.

10. The X-ray detector module of claim 1, wherein each respective forwarding circuit of the number of forwarding circuits is constructed to be integrated into a respective evaluation circuit of the plurality of evaluation circuits.

11. The X-ray detector module of claim 1, wherein each respective forwarding circuit of the number of forwarding circuits takes a form of a component constructed separately from the evaluation circuits of the plurality of evaluation circuits.

12. A medical imaging device, comprising:
    at least one detector including at least one of the X-ray detector module of claim 1, and an X-ray source, arranged opposite the at least one detector, constructed to expose the at least one converter coupled to the plurality of evaluation circuits to X-ray radiation.

13. The medical imaging device of claim 12, wherein the medical imaging device takes the form of a computed tomography device.

14. A method for operating an X-ray detector module according to claim 1, the method comprising:
- exposing at least one converter circuit of the X-ray detector module, coupled to a plurality of evaluation circuits of the X-ray detector module, to X-ray radiation via an X-ray source;
- recording a measured data set for each evaluation circuit of the plurality of evaluation circuits, based on the incident X-ray radiation; and
- forwarding the measured data sets via a forwarding circuit of a number of forwarding circuits of the X-ray detector module, wherein
- a measured data set of the measured data sets, from a first evaluation circuit of the plurality of evaluation circuits is received via of a first data input of the forwarding circuit, and a forwarded measured data set, from a further forwarding circuit of the number of forwarding circuits, is received via a second data input; and
- the measured data sets that received via at least one of the first data input and second data input are forwarded to a receiving circuit via the forwarding circuit over a common data output.

15. The X-ray detector module of claim 2, wherein the number of forwarding circuits includes a plurality of forwarding circuits, wherein forwarding circuits of the plurality of forwarding circuits are connected one after another in a manner of a string of beads, wherein a forwarding circuit of the plurality of forwarding circuits receives measured data sets forwarded at most from one further forwarding circuit.

16. The X-ray detector module of claim 2, wherein the number of forwarding circuits includes a plurality of forwarding circuits, connected in a tree-like set-up, wherein at least some of the plurality of forwarding circuits are coupled in a signal-carrying manner, by way of two separate data inputs of the at least some of the forwarding circuits, to at least two further forwarding circuits of the plurality of forwarding circuits.

17. The X-ray detector module of claim 2, wherein a serializer/deserializer interface is used for data transmission between a respective forwarding circuit of the number of forwarding circuits and the coupled respective receiving circuit.

18. The X-ray detector module of claim 2, wherein an LVDS line is used for data transmission of the measured data sets between a respective forwarding circuit of the number of forwarding circuits and the coupled respective receiving circuit.

19. The X-ray detector module of claim 2, wherein a respective forwarding circuit of the number of forwarding circuits comprises a network router or a network switch.

20. The X-ray detector module of claim 19, wherein for data transmission of the measured data sets between a respective forwarding circuit of the number of forwarding circuits and the receiving circuit coupled thereto, a network protocol is used.

21. The X-ray detector module of claim 2, wherein each respective forwarding circuit of the number of forwarding circuits is constructed to be integrated into a respective evaluation circuit of the plurality of evaluation circuits.

22. The X-ray detector module of claim 2, wherein each respective forwarding circuit of the number of forwarding circuits takes a form of a component constructed separately from the evaluation circuits of the plurality of evaluation circuits.

23. A medical imaging device, comprising:
- at least one detector including at least one of the X-ray detector module of claim 2, and
- an X-ray source, arranged opposite the at least one detector, constructed to expose the at least one converter coupled to the plurality of evaluation circuits to X-ray radiation.

24. The medical imaging device of claim 23, wherein the medical imaging device is a computed tomography device.

* * * * *